United States Patent [19]

Mukai et al.

[11] Patent Number: 5,074,397
[45] Date of Patent: Dec. 24, 1991

[54] ROTARY INDEX APPARATUS

[75] Inventors: Takahiro Mukai; Toshikazu Nakayama; Shoji Yamagishi, all of Kanagawa, Japan

[73] Assignee: Kirin Techno-System Corporation, Japan

[21] Appl. No.: 560,447

[22] Filed: Jul. 31, 1990

[30] Foreign Application Priority Data

Aug. 3, 1989 [JP] Japan ............................ 1-201609

[51] Int. Cl.$^5$ ............................................. B65G 29/00
[52] U.S. Cl. ............................ 198/343.1; 198/476.1; 198/478.1; 198/802
[58] Field of Search ............... 198/343.1, 478.1, 474.1, 198/476.1, 477.1, 802

[56] References Cited

U.S. PATENT DOCUMENTS

| | | | |
|---|---|---|---|
| 2,382,087 | 8/1945 | Miller | 198/343.1 |
| 2,415,997 | 2/1947 | Eldred | 198/474.1 X |
| 2,468,255 | 4/1949 | Dunn | 198/474.1 X |
| 3,256,970 | 6/1966 | Fievet | 198/343.1 |
| 3,422,966 | 1/1969 | Iansons | 198/343.1 |
| 4,753,336 | 6/1988 | Taylor et al. | 198/343.1 |

FOREIGN PATENT DOCUMENTS 2905376 8/1980 Fed. Rep. of Germany .

Primary Examiner—D. Glenn Dayoan
Attorney, Agent, or Firm—Ladas & Parry

[57] ABSTRACT

A rotary index apparatus for treating an article at predetermined positions while the article is conveyed, has an indexing conveyor unit with a plurality work support tables, a rotary disk unit rotated at a constant speed and having a plurality of swinging arms at its periphery for provision of an intermittent motion to the work support tables, and a cam unit having a guide passage, which engages with a cam follower of each swinging arm for provision of a special swinging motion. Thus, the work support table are stopped at predetermined positions for a predetermined time while the work support tables is conveyed along the indexing conveyor unit.

19 Claims, 9 Drawing Sheets

ROTARY INDEX APPARATUS

BACKGROUND OF THE INVENTION

The present invention relates to a rotary index system for stopping, at predetermined angle positions, articles to be inspected or treated which are being conveyed along a circular track and inspecting or treating the articles at these positions.

A rotary index apparatus is generally known to carry out a series of workings comprising, such as, the steps of receiving articles continuously conveyed, conveying the articles along a circular track, stopping the articles at predetermined angle positions during the conveyance thereof, inspecting the articles during the stay at those positions, and welding the articles to the other parts or members or assembling the articles in the other parts or members.

As one typical example of such rotary index apparatus, there may be proposed a bottle inspection apparatus. A conventional bottle inspection apparatus of one example of the rotary index apparatus includes a main disk plate, around which a plurality of recessed portions for accommodating beer bottles, for example, are formed. Two holding arms are disposed opposite to the recessed portions. The beer bottles conveyed along a conveyor are fed into the recessed portions by means of screw conveyors and accommodated therein. In accordance with the rotation of the disk plate, the beer bottles thus fed in the recessed portions are then conveyed to portions at which the beer bottles are inspected by means of cameras which inspect the beer bottles. The beer bottles after the inspection are transferred with equal intervals to a discharge conveyor and the beer bottles discriminated to be fault are taken out on a reject table by a proper rejecting means.

During the processes described above, the beer bottles are transferred from the screw conveyor to the main disk plate now being in a stationary condition and then intermittently conveyed to respective inspection stations by the intermittent rotation of the disk plate by predetermined angles. When the beer bottle reaches the camera inspection position, the inspection is performed with the disk plate of circumferential revolution stopped and the beer bottle rotated.

In another aspect, in a conventional rotary index apparatus for assembling precision parts or the like, the inspection or welding working of the precision parts is performed by mounting parts to be treated on predetermined positions of an indexing table intermittently rotated manually or automatically and by stopping intermittently the indexing table to a plurality of treating stations disposed along the periphery of the indexing table.

However, in the conventional rotary index apparatus of the characters described above, the main disk plate or the indexing table receives the articles to be treated from the conveyor with the rotation stop condition and transfers the articles treated at the respective stations to the discharge conveyor with the rotation stop condition. Therefore, the article cannot be smoothly conveyed in or out from the main disk plate or indexing table and, in an adverse case, the article may fall down, thus being difficult to stably operate the whole apparatus. In addition, the intermittently repeated rotations or stoppings of the disk plate or the indexing table imparts mechanical impacts to the disk plate or the indexing table at the respective rotation stopping and starting times. This also involves problems of durability of the apparatus and the operation speed thereof is not made high. This constitutes a significant problem for the apparatus.

SUMMARY OF THE INVENTION

An object of the present invention is to substantially eliminate the defects or drawbacks encountered to the prior art described above and to provide a rotary index apparatus capable of smoothly receiving articles to be treated and transferring externally the same after the necessary treatment and achieving a high speed operation and an improved durability of an apparatus itself.

This and other objects can be achieved according to the present invention by providing a rotary index apparatus in which at an article to be treated is received at an article in-conveyance position, stopped at a predetermined position to be subjected to necessary treatment and transferred externally at an article out-conveyance position, the rotary index apparatus comprising an indexing conveyor means provided with a guide member along which the article received by the indexing conveyor means is conveyed with the article supported, a rotary disk means operatively connected to the indexing conveyor means for driving the same and a cam means operatively connected to the rotary disk means for causing an intermittent motion to the rotary disk means, the rotary disk means including a disk plate and a plurality of swinging arms swingably secured to an outer peripheral portion of the disk plate, each of the swinging arm being provided with a cam follower and provided with a first engaging structure formed at a front end of the swinging arm, the indexing conveyor means with the guide member for guiding the revolution of the article including a plurality of work support tables arranged to a peripheral portion of the guide member, each of the work support table being arranged in positional correspondence to a respective one of the swinging arms of the rotary disk means and including a second engaging structure to be engaged with the first engaging structure of the swinging arm, and the cam means including a guide passage with which the cam follower of the swinging arm is engaged and which has a wave shape provided with predetermined alternately repeated wave troughs and wave crests so as to vanish a force for moving the second engaging structure in a revolving direction when the cam follower approaches a predetermined portion of the wave trough of the guide passage and to cause a force for moving the second engaging structure in the revolving direction when the cam follower passes the predetermined portion of the wave trough of the guide passage.

In preferred embodiments, in one aspect, the first engaging structure is formed by biforked portion of the swinging arm and the second engaging structure is a guide roller secured to a lower portion of the work support table. The cam means includes a cam plate and the guide passage is a cam groove formed on the cam plate, the cam follower of the swinging arm being engaged with the cam groove so as to cause an intermittent movement of the work support table through the engagement between the first and second engaging structures. The numbers of the wave troughs and wave crests of the guide passage correspond to treating stations arranged along the periphery of the guide member of the indexing conveyor means.

In another aspect of the preferred embodiments, the disk plate of the rotary disk means comprises a polygonal plate having side surface including a plurality of flat portions and the swinging arms are secured to the flat portions of said polygonal plate, respectively, each of the swinging arm comprising a bearing housing mounted to the corresponding flat surface, a bearing incorporated in the bearing housing and having an inner axial hollow portion, a cam follower support including a cam follower to be engaged with the guide passage of the cam plate of the cam means and a rotating shaft to be rotatably fitted into the axial hollow portion of the bearing of the bearing housing, and a linear guide table including the first engaging structure. The work support table comprises a rotating plate having a work rest member on which the article is rested, a roller means mounted to the rotating plate, the roller means being engaged with the guide member of the indexing conveyor means, and a shaft extending downwardly from a lower surface of the rotating plate, the shaft being provided with the second engaging structure. The cam plate comprises a first and a second cam plate members arranged vertically in an angularly offset manner. In this aspect, the first engaging structure comprises a bearing incorporated in the linear guide table and having an inner axial hollow portion and the second engaging structure comprises an extending front end portion of the shaft having a shape to be fitted into the axial hollow portion of the bearing of the linear guide table.

The cam follower comprises a first and a second cam follower members arranged vertically, the first and second cam plate members having side surfaces formed as guide passages engaged with the first and second cam follower members, respectively, and having wave shapes respectively provided with predetermined alternately repeated wave troughs and wave crests so as to vanish a force for moving the second engaging structure in a revolving direction when one of the cam follower members approaches a predetermined portion of the wave trough of the guide passage and to cause a force for moving the second engaging structure in the revolving direction when the cam follower member passes the predetermined portion of the wave trough of the corresponding guide passage. The wave shapes of the guide passages of the first and second cam plate members are arranged in an angularly offset manner.

According to the characters described above of the rotary index apparatus according to the present invention, the guide member is disposed in association with the article, support tables are arranged along the guide member with equal spaces therebetween. The article indexing conveyor means receives the article at the article in-conveyance and out-conveyance positions while rotating the work support tables, and the work support tables stop their rotation at the treating stations for a predetermined time.

As described above, the work support tables receive and transfer the articles at the article in- and out-conveyance positions while rotating along the outer periphery of the indexing conveyor means, thus smoothly treating the articles and the revolution of the work support tables is stopped at the treating stations.

BRIEF DESCRIPTION OF THE DRAWINGS

For a better understanding of the present invention and to show how the present invention is carried out, reference is now made to, by way of preferred examples, the accompanying drawings, in which.

DESCRIPTION OF THE PREFERRED EMBODIMENTS

One embodiment according to the present invention applied to a bottle inspection machine will be described hereunder with reference to the accompanying drawings.

Figure 1:
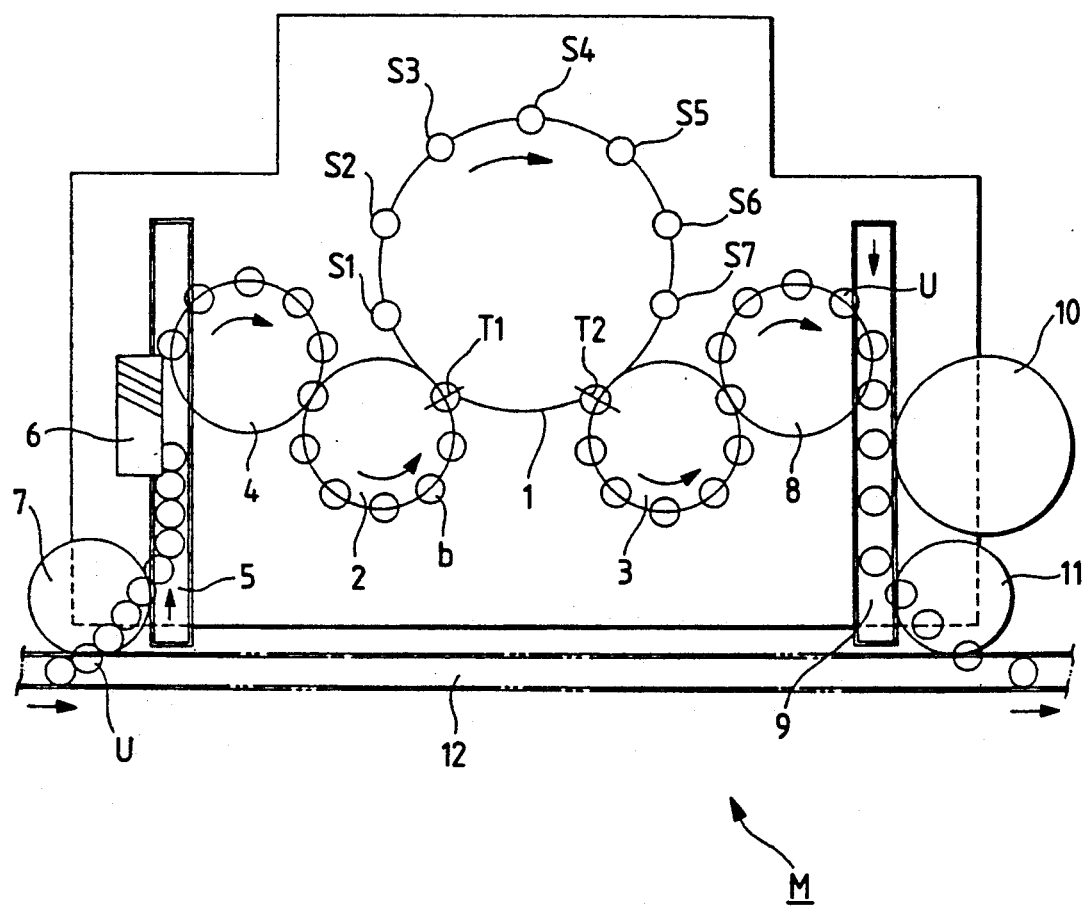
FIG. 1 is a brief plan view of a bottle inspection machine to which the present invention is applied.

Referring to FIG. 1, a bottle inspection machine M including a rotary index apparatus according to the present invention is provided with a circular bottle inspection unit 1 as an indexing conveyor. A first infeed turret 2 is disposed adjacent to the bottle inspection unit 1 and a first out-feed turret 3 is also disposed adjacent to the bottle inspection unit 1 in opposition to the in-feed turret 2. Adjacent to the first in-feed turret 2 is disposed a second in-feed turret 4 to which beer bottles U, as articles to be treated, continuously conveyed by a conveyor 5 are fed with predetermined intervals by an in-feed screw 6 arranged adjacent to the conveyor 5.

The beer bottles U are conveyed by a main conveyor 12 into the conveyor 5 through a guide member 7 disposed between the main conveyor 12 and the conveyor 5. The beer bottles U are then fed to the first in-feed turret 2 through the second in-feed turret 4. The beer bottles U supported by the first in-feed turret 2 are transferred to the bottle inspection unit 1 at an in-conveyance portion T1. The thus transferred beer bottles U are inspected at inspection stations provided as treatment stations S1, S2 . . . S7 along the circular track of the bottle inspection unit 1 and, thereafter, are conveyed out from the inspection unit 1 to the first out-feed turret 3 at a bottle out-conveyance portion. The beer bottles U are then transferred to a second out-feed turret 8 located adjacent the first out-feed turret 3. The beer bottles U supported by the second out-feed turret 8 are transferred to a conveyor 9 at a predetermined portion of the second out-feed turret 8. The beer bottles U are then conveyed towards the main conveyor 12 and guided by the guide member 11. Bottles discriminated to be fault by the inspection of the respective stations of the bottle inspection unit 1 are discharged by a discharging device, not shown, to a reject turn table disposed along the conveyor 12.

The structure of the bottle inspection unit 1 constructed as a rotary index apparatus will described hereunder.

Figure 2:
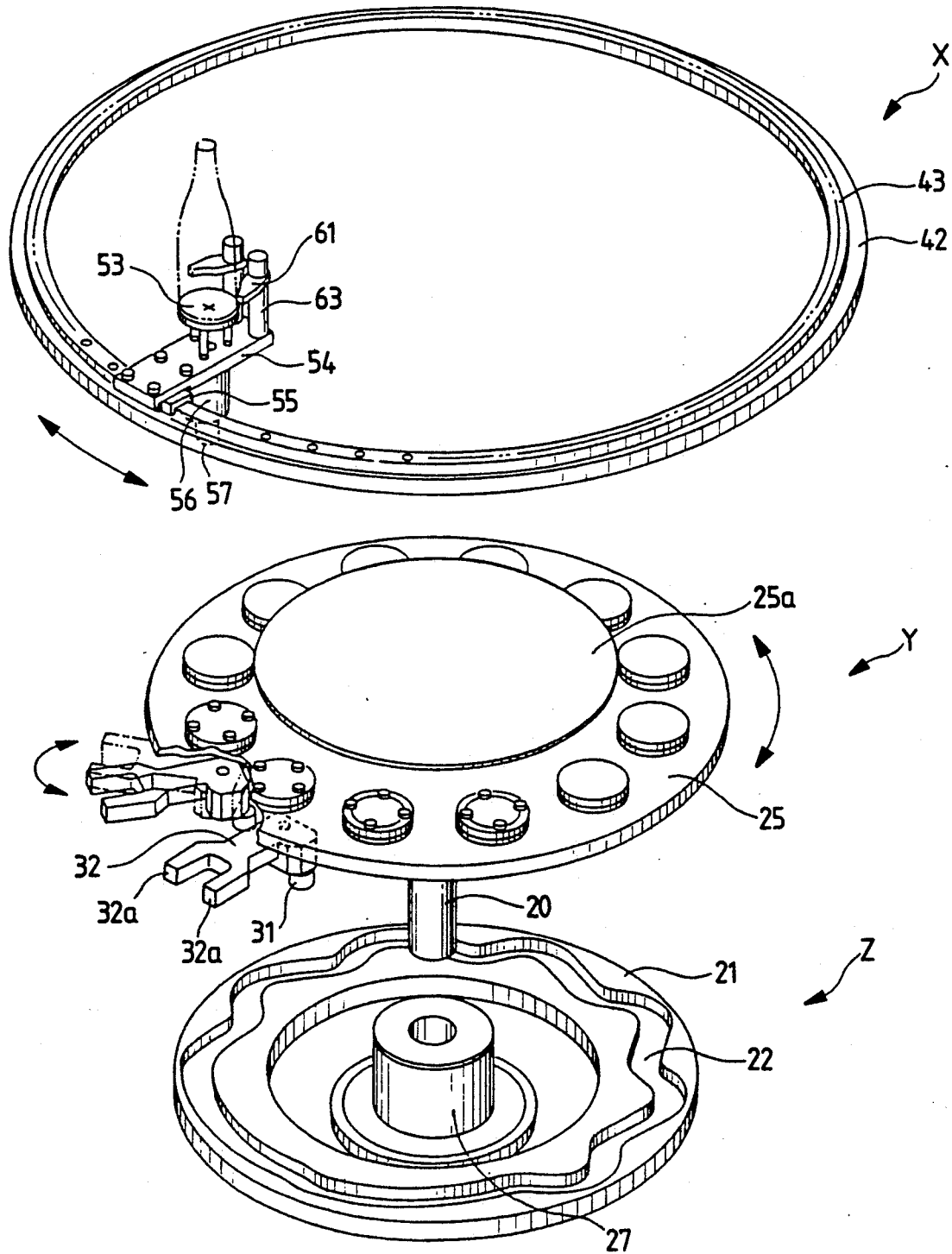
FIG. 2 is a disassembled perspective view of a rotary index apparatus according to one embodiment of the present invention.

As shown by a disassembled perspective view of FIG. 2, the rotary index apparatus of a first embodiment of the present invention comprises a circular indexing conveyor unit X equipped with a plurality of work support tables 54 as base tables for supporting articles to be treated and conveying the articles along a circular track formed on the upper surface of the indexing conveyor unit X, a rotary disk unit Y equipped with a plurality of swinging arms 32 and a cam unit Z including a cam member on which a cam groove 22 is formed as a guide passage for guiding the swinging arms 32. A cam follower 31 is provided at the lower portion of each of the swinging arms 32 and a guide roller 57 is provided at the lower portion of the work support table 54. The cam follower 31 and the guide roller 57 are engaged respectively with the cam groove 22 and a forked portion of the arm 32 when the indexing conveyor unit X, the rotary disk unit Y and the cam unit Z are assembled as the rotary index apparatus.

Figure 3:
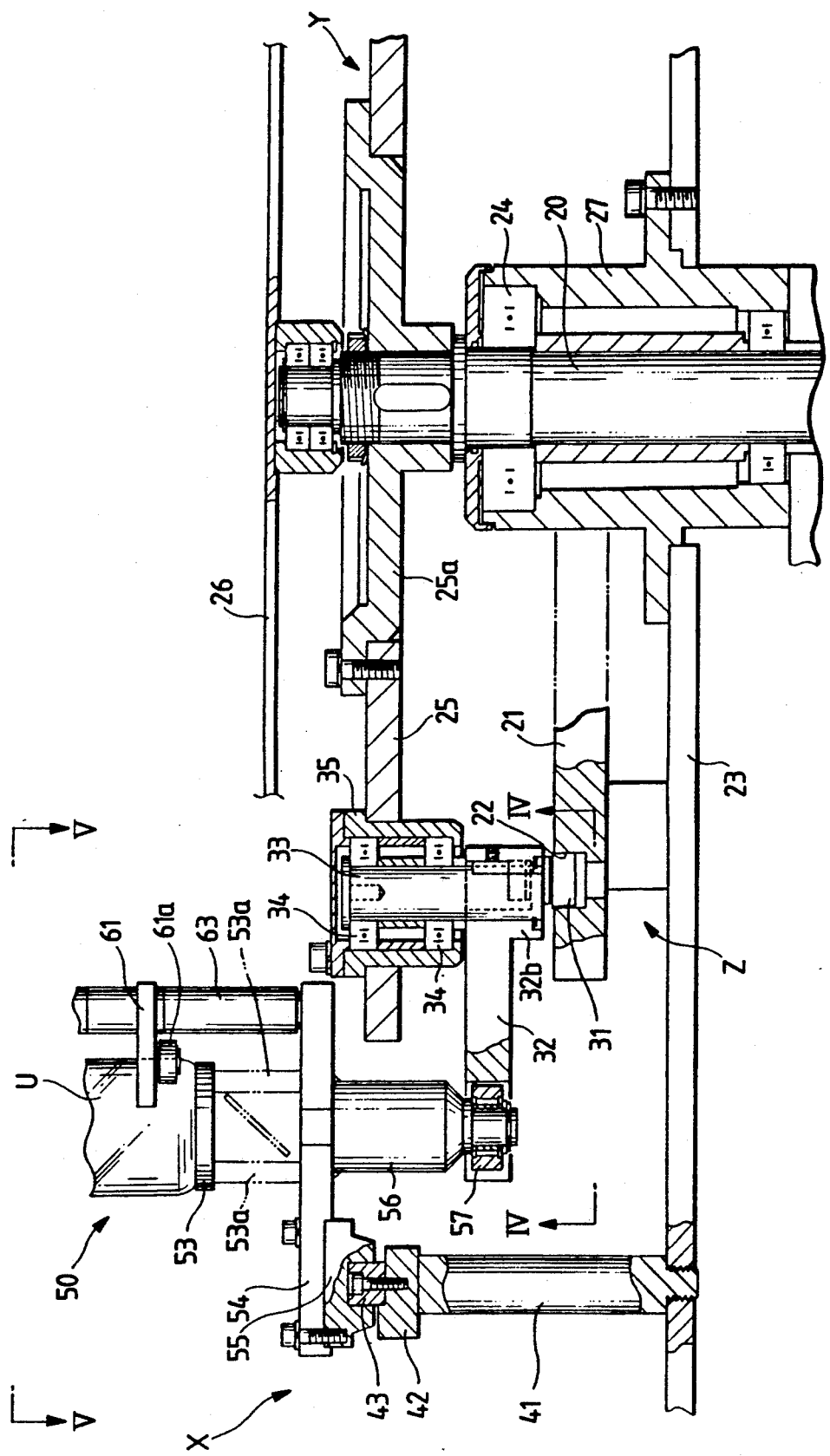
FIG. 3 is a view showing an elevational section, partially cutaway, of the rotary index apparatus shown in FIG. 2.

Referring to FIGS. 2 and 3, the rotary index apparatus, i.e. bottle inspection unit 1, is provided with a central rotation shaft 20 which is continuously rotated by a main motor, not shown, in synchronism with the rotations of the respective turrets 2, 4, 3 and 8.

A bottom plate 23 is secured to a bearing holder 27 of the rotation shaft 20. The cam unit Z comprises, as base member, a plate 21 on which the cam guide passage, i.e. groove in this embodiment, is formed. The cam groove plate 21 is secured above the bottom plate 23. The cam groove 22 is formed at the peripheral side portion of the cam groove plate 21 and the rotary disk unit Y is disposed above the cam groove plate 21. The rotary disk unit Y comprises a rotary disk plate 25 having a peripheral portion along which a plurality of equally spaced swinging arms 32 are arranged in the radial direction of the rotary disk plate 25. The number of the swinging arms 32 corresponds to the number of the work support tables 54.

The central portion of the rotary disk plate 25 is secured to the upper end of the rotation shaft 20 through an attachment rotary disk plate 25a to thereby continuously rotate the rotary disk unit Y at a constant speed in accordance with the rotation of the rotation shaft 20.

A cover 26 is disposed above the rotary disk unit Y to cover the central portion thereof.

Figure 4:
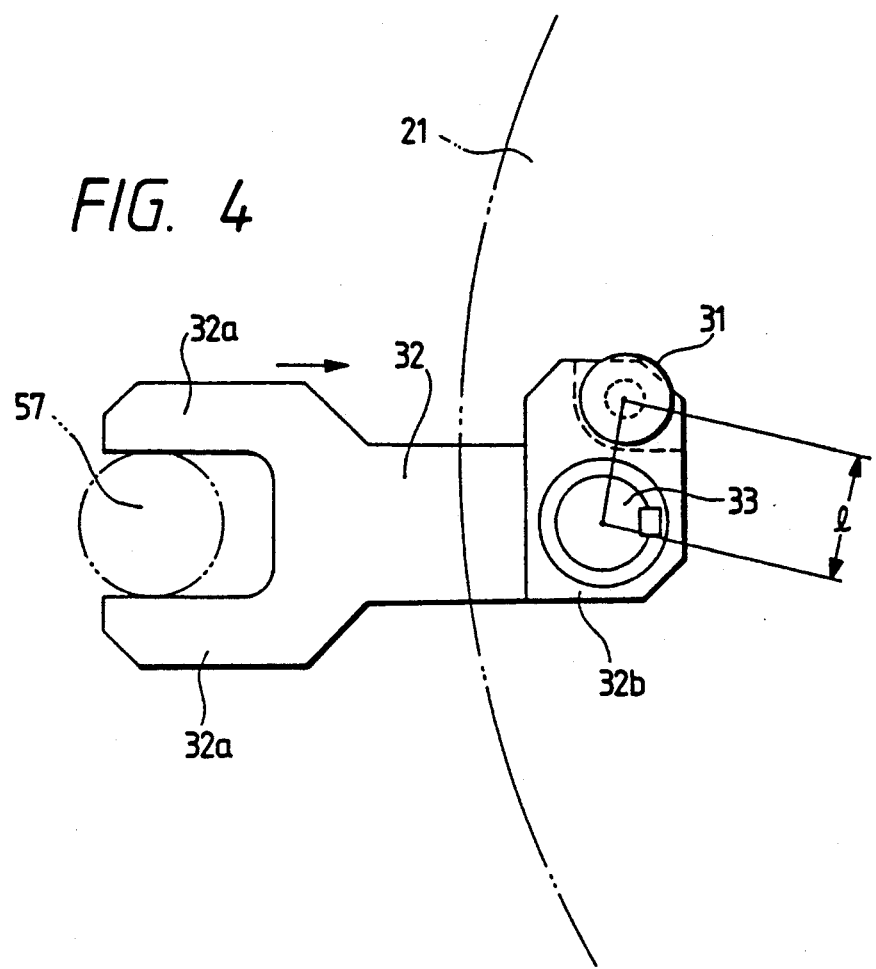
FIG. 4 is a sectional view taken along the line IV—IV shown in FIG. 3.

Each of the swinging arms 32 arranged with equal spaces to the peripheral portion of the rotary disk unit Y is secured to the lower end of a fulcrum shaft 33 suspended in a supported manner from a bearing unit 35 including bearing 34. As shown in FIG. 4, a base portion 32b of each of the swinging arms 32 is provided with a cam follower 31 at a portion apart from a distance l from the center of the fulcrum shaft 33.

The cam follower 31, as shown in FIG. 3, extends slightly downward from the lower surface of the base portion 32b and is engaged with the cam groove 22 formed in the cam groove plate 21. The shape of the cam groove 22 will be described hereinafter.

As shown in FIGS. 2 and 4, the front end portion of the swinging arm 32 has two arms 32a, 32a in a biforked form, which is referred to as a first engaging structure and a guide roller 57 formed as a second engaging structure at the lower portion of the work support table 54 of the indexing conveyor unit X (FIG. 3) is inserted between the two arms 32a, 32a. As shown in FIG. 4, the contact engaging surfaces between the first and second engaging structures can be made slidably movable in the radial (arrowed) direction during the acceleration, deceleration and stop motion of the work.

Figure 5:
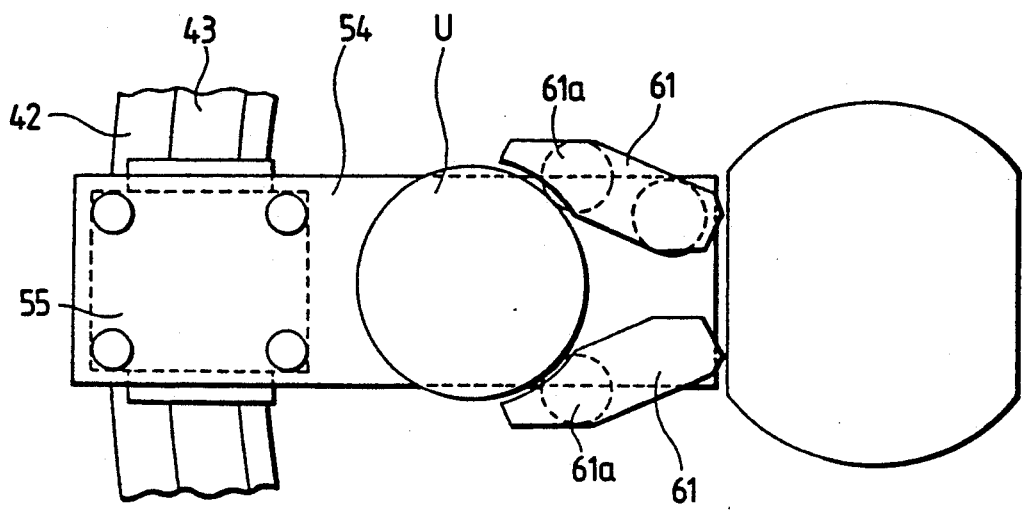
FIG. 5 is a sectional view taken along the line V—V shown in FIG. 3.

As shown in FIG. 3, the bottom plate 23 to which the cam groove plate 21 is secured is provided with an outer peripheral portion on which a plurality of support columns 41 are circularly arranged in a standing manner. The indexing conveyor unit X on which the articles to be treated are mounted and fed along the circular track is mounted on the upper end surfaces of the support columns 41. Namely, as shown in FIGS. 3 and 5, a ring shaped rail base 42 is mounted on the upper ends of the columns 41 and a ring shaped guide rail 43 is secured to the rail base 42. With the guide rail 43 is slidably engaged with a sliding member 55 to which one end of the work support table 54 is secured, and to the work support table 54 is mounted a work rest table 53 through three columns 53a. Beer bottles U, for example, are rested on the work rest table 53. Guide plates 61 and 61, guide rollers 61a and 61a are disposed to the work rest table 53 through standing columns 63 and 63 for preventing the bottles from being fallen down.

The work rest table 53 is provided with a rear surface from which a round bar 56 projects downwardly and the rotating roller 57 is secured to the lowermost end of the round bar 56 to be rotatable. As described before, the roller 57 as the second engaging structure is inserted into the two arms 32a referred to as the first engaging structure of each of the swinging arms 32 arranged along the outer peripheral portion of the rotary disk unit Y. Accordingly, the revolution power of each of the swinging arms 32 is transmitted to the guide roller 57 of the indexing conveyor unit X while being affected with the influence of the shape of the cam groove 22, which will be described in detail hereinafter, whereby the work support tables 54 perform the revolution motion as well as the predetermined intermittent movement under the guidance of the guide rail 43.

The guide rail 43 has a circular track for conveying the beer bottles mounted thereon.

The shape of the cam groove 22 formed in the cam member of the cam unit Z and the loci of the movements of the cam follower 31 and the guide roller 57 corresponding to the revolution of the article when the cam follower 31 engages with the cam groove 22 and the rotary disk unit Y is rotated with a constant speed will be described in detail hereinbelow with reference to FIGS. 6 and 7.

Figure 6:
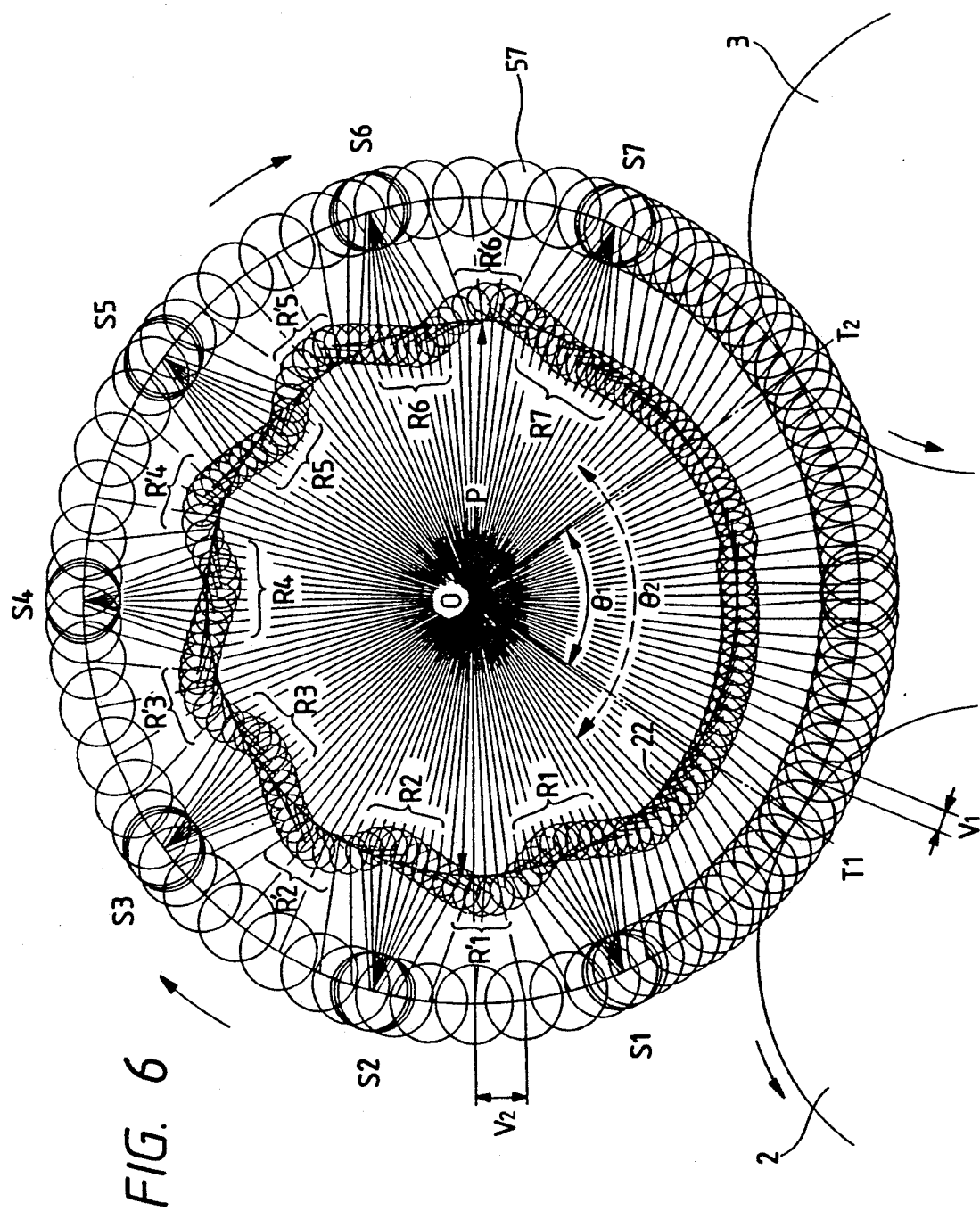
FIG. 6 is a view for the explanation of the movement loci of a cam groove and members associated therewith.

FIG. 6 is a view of the cam groove 22 upon the view from the upper side of the inspection apparatus 1. Referring to FIG. 6, the locus of the circular motion of the outermost periphery, with the point 0 as the center of the motion, represents the locus of the movement (corresponding to the movement of the article to be treated) of the guide roller 57 of the indexing conveyor unit X. A ring-like groove formed inside the loci of this largest circular motion and having a wave shape provides the shape of the cam groove 22. A plurality of overlapped circles described in the width of the cam groove 22 represent the loci of the movement of the cam follower 31. The circle having a diameter P represents the locus of the movement of the fulcrum shaft 33 secured to the rotary disk unit Y and performing the uniform speed circular movement. A plurality of straight lines equally spaced and radially extending from the center 0 towards the circular locus of the fulcrum shaft 33 represent the fact that the fulcrum shaft 33 is rotated with a constant speed on the circle having the diameter P.

Figure 7:
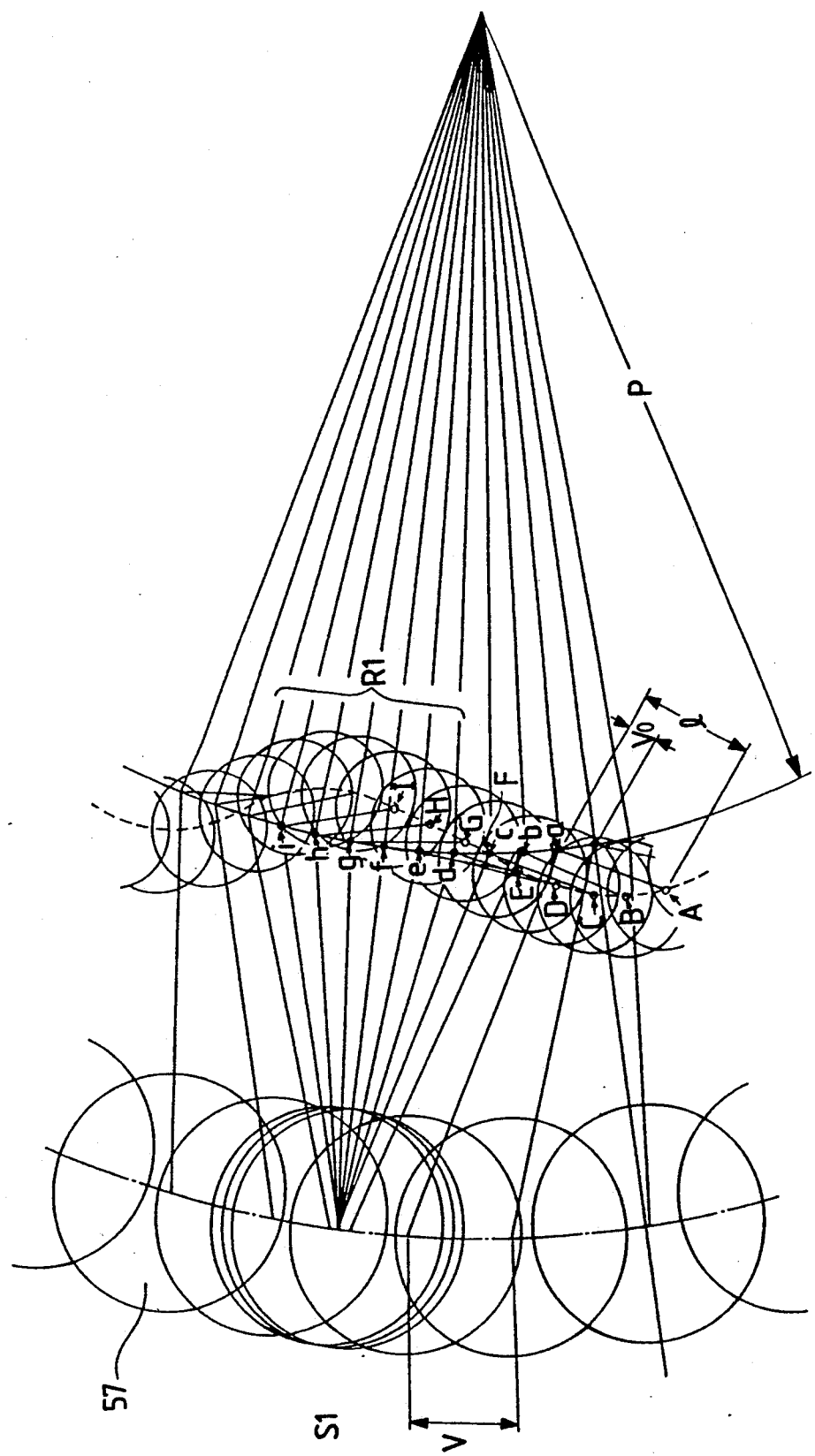
FIG. 7 is an enlarged view of a part of FIG. 6 near an inspection station S1.

Referring to FIG. 7, for example, the cam follower is positioned in the cam groove at the position by a distance l rearwardly apart from an optional point (a position of the fulcrum shaft 33) on the circumference of the circle having the diameter P. Furthermore, in FIG. 7, a distance v between the moving loci of the adjacent guide rollers 57 represents a speed corresponding to a constant speed $V_0$ of the fulcrum shaft 33.

As shown in FIG. 6, the shape of the cam groove has substantially a gentle arcuate slope in an angle range $\theta 2$ which is slightly larger than an angle $\theta 1$ between the article in-conveyance position T1 and the article out-conveyance position T2. The cam groove has also a wave shape (having wave troughs R1, R2, R3, R4, R5, R6 and R7, and wave crests R'1, R'2, R'3, R'4, R'5, R'6 and R'7) in an alternately repeated manner between a position just before a position of the station S1 at which the article stops for a predetermined time and a position from which the article is transferred apart from the station S7. Namely, the wave shape of the cam groove is formed in connection with the positions of the stations S1 to S7 so that the wave troughs substantially correspond to the location of the stations, respectively.

The detailed motion of the cam unit Z at a portion near the station S1 will be described hereunder.

When the cam follower 31 approaches the trough R1, the guide roller 57 stops the revolution at a portion of the station S1. During this operation, the rotary disk unit Y is rotated with a constant speed and the fulcrum shaft 33 secured to the rotary disk unit Y describes circular movement loci as shown in FIG. 7 with solid lines c to i and the movement of the center of the cam follower 31 describes the movement loci C to I shown with dotted lines. During this operation, the swinging arm 32 moves as if the arm 32 swings in a sliding manner with the station S1 as the center of the rotation and a force for causing the guide roller 57 of the indexing conveyor unit X to revolve is not applied. In the next step, when the cam follower 31 just passes the end portion of the wave trough R1, the force to rapidly revolve the guide roller 57 is applied by the engagement of the swinging arm 32 and the guide roller 57 is operated with an accelerated speed. The operation speed of the guide roller 57 reaches the maximum speed at the central portion of the wave crest R'1 and, thereafter, the operation speed thereof is decreased when the cam follower 31 approaches the next wave trough R2. In thus manner, the revolution of the guide roller 57 stops when the cam follower 31 reaches the station S2.

It will be easily noted that substantially the same motion or operations, i.e. acceleration, deceleration and stop motions, of the cam follower 31 and the guide roller 57 are performed with respect to the other stations S3 to S7. Finally, the uniform speed motion is carried out and the article is transferred externally from the out-conveyance portion T2. The wave shape of the cam groove is made relatively gentle at the station S7 for the provision of the constant speed area for externally smoothly conveying the article such as a beer bottle.

A series of operations of the rotary index apparatus of one embodiment described above according to the present invention will be described hereunder.

The beer bottles U conveyed by the first in-feed turret 2 (FIG. 1) are transferred on the work rest table 53. At this moment, the circumferential speed of the work receiving side at the in-conveyance position T1 is made substantially equal to that of the first in-feed turret 2 to smoothly carry out the transfer of the beer bottles.

The beer bottles U thus transferred are conveyed with substantially the constant speed for a time being and when each of the beer bottles approaches a portion just before the station S1, the conveying speed decreases and stops completely at the station S1. After the elapsing of the predetermined time, the bottle is again conveyed towards the station S2 while being accelerated. The conveying speed is decelerated from a time when the bottle passes the substantially intermediate portion between the stations S1 and S2 and the bottle completely stops at the station S2. Substantially the same motion or operation, i.e. acceleration, deceleration and stop motion, of the bottle movement or conveyance is carried out at the other stations S3 to S7. Finally, the uniform speed motion is achieved and the article is transferred from the out-conveyance portion T2 to the first out-feed turret 3 and then conveyed externally. At this time, as stated before, the circumferential speed of the work transferring side and that of the first out-feed turret 3 are substantially equal to each other for the smooth transferring of the beer bottle.

The inspection unit arranged at the periphery of the indexing apparatus for carrying out the intermittent motion described above will be operated as follows. For the sake of convenience of explanation, an example provided with five stations will be referred to hereunder with reference to FIG. 8.

Figure 8:
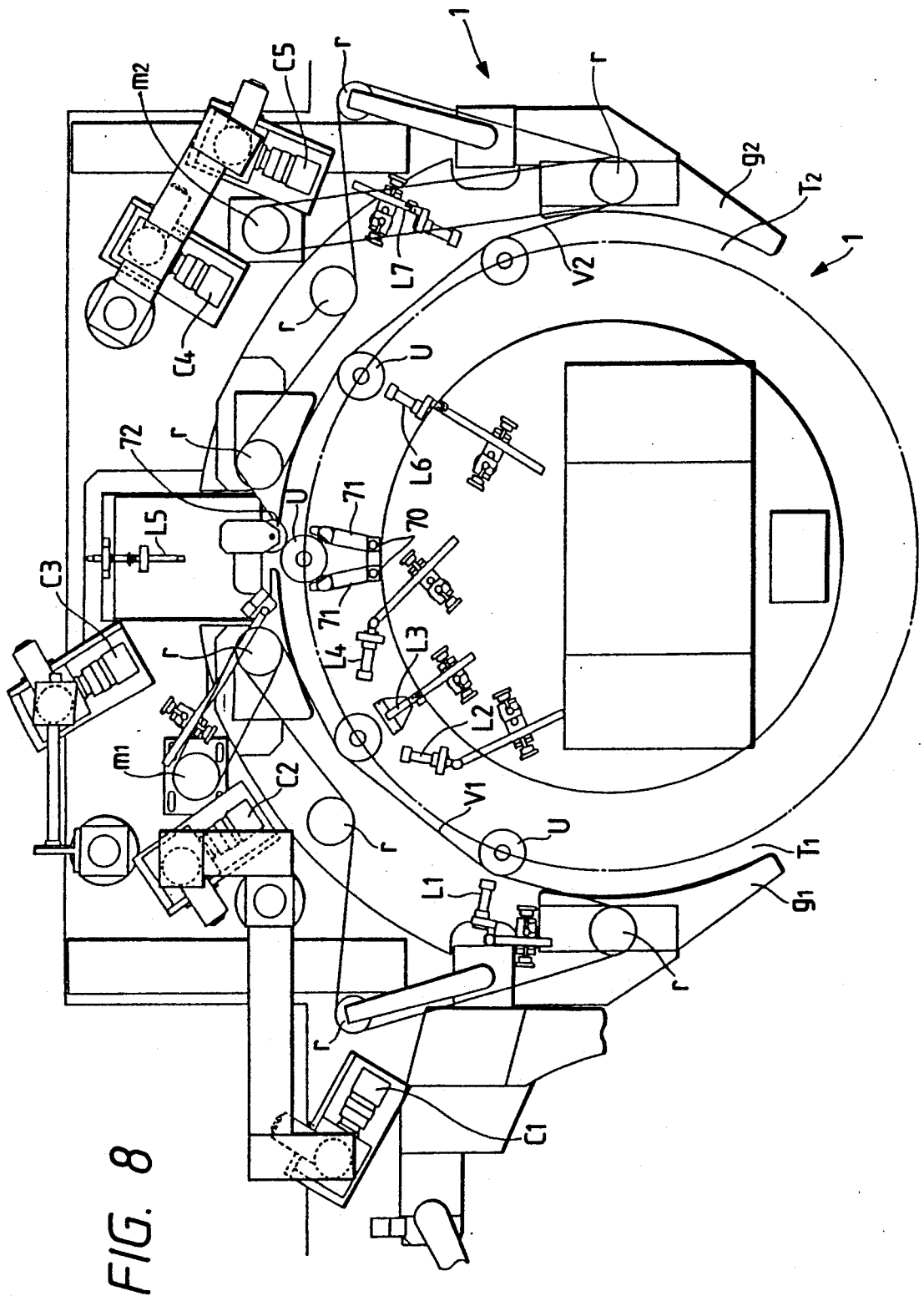
FIG. 8 is a brief plan view of an inspection unit arranged adjacent the rotary index apparatus.

Referring to FIG. 8, cameras C1, C2, C3, C4 and C5 are set to positions for the corresponding inspection stations, respectively. Lighting means L1, L2, L3, L4, L5, L6 and L7 are also set in relation with the cameras C1 to C5 for lighting the beer bottle as article to be inspected. The circumferential movement, i.e. revolution, of the beer bottles rested on the work rest tables 53 stop at the inspecting positions of the respective inspection stations S1 to S5 and the bottles are subjected to inspection by the cameras C1 to C5 under the lighting of the lighting means L1 to L7 for inspecting cutouts of mouth portions of the bottles, injury or dirt of the bottle, for example.

Namely, the beer bottles U transferred by the first in-feed turret 2 (FIG. 1) are guided by a guide plate $g_1$ and transferred smoothly on the work rest tables 53. Thereafter, the bottles are inspected at the respective inspection stations S1 to S5 and, then, guided by a second guide plate $g_2$ to the first out-feed turret 3 from which the bottles are conveyed externally. Rotating belts V1 and V2 for rotating the beer bottles along the circular track are arranged between the in-conveyance position T1 and the out-conveyance position T2 and the rotating belts V1 and V2 are driven by corresponding motors $m_1$ and $m_2$ with predetermined speeds, respectively, and guided by guide rollers r, r ... r. A roller 72 is disposed at a portion at which the belts V1 and V2 are adjacent. The roller 72 is provided for the station S3, at which the shell of the beer bottle is released from the belts V1 and V2 and the released shell of the beer bottle is inspected by the corresponding camera C3. Namely, the shell portion of the beer bottle is covered by the rotating belts V1 and V2 at the other stations S1, S2, S4 and S5, but the shell is released from the belts by being rotated by the roller 72, thus being capable of inspecting the shells of the beer bottles.

A second embodiment according to the present invention will be described hereunder with reference to FIGS. 9 and 10 and the basic technical concept of the second embodiment is substantially identical to that of the first embodiment.

The main difference between the first embodiment and the second embodiment resides in the structures of the cam members and, in the second embodiment, the cam groove plate of the first embodiment is substituted with vertically parallelly overlapped two cam plates each having wave-shape cam surface, i.e. side surface against which a cam follower abuts. According to this structure, it is possible to attain substantially the same cam function as that of the first embodiment and, in addition, it is possible to provide a structure with substantially no vibration or shock and, hence, to provide a rotary index apparatus capable of being smoothly operated with a high speed.

Moreover, in the second embodiment, a linear guide member slidable in a radial direction of the cam plate and a rotatable bearing means are utilized in place of the biforked member of the swinging arm in the first embodiment. Furthermore, the guide rail of the indexing conveyor unit and the members associated therewith in the first embodiment are substituted with a guide groove and associated members in the second embodiment.

The details of the specific structure of the second embodiment will be further described hereunder.

Figure 9:
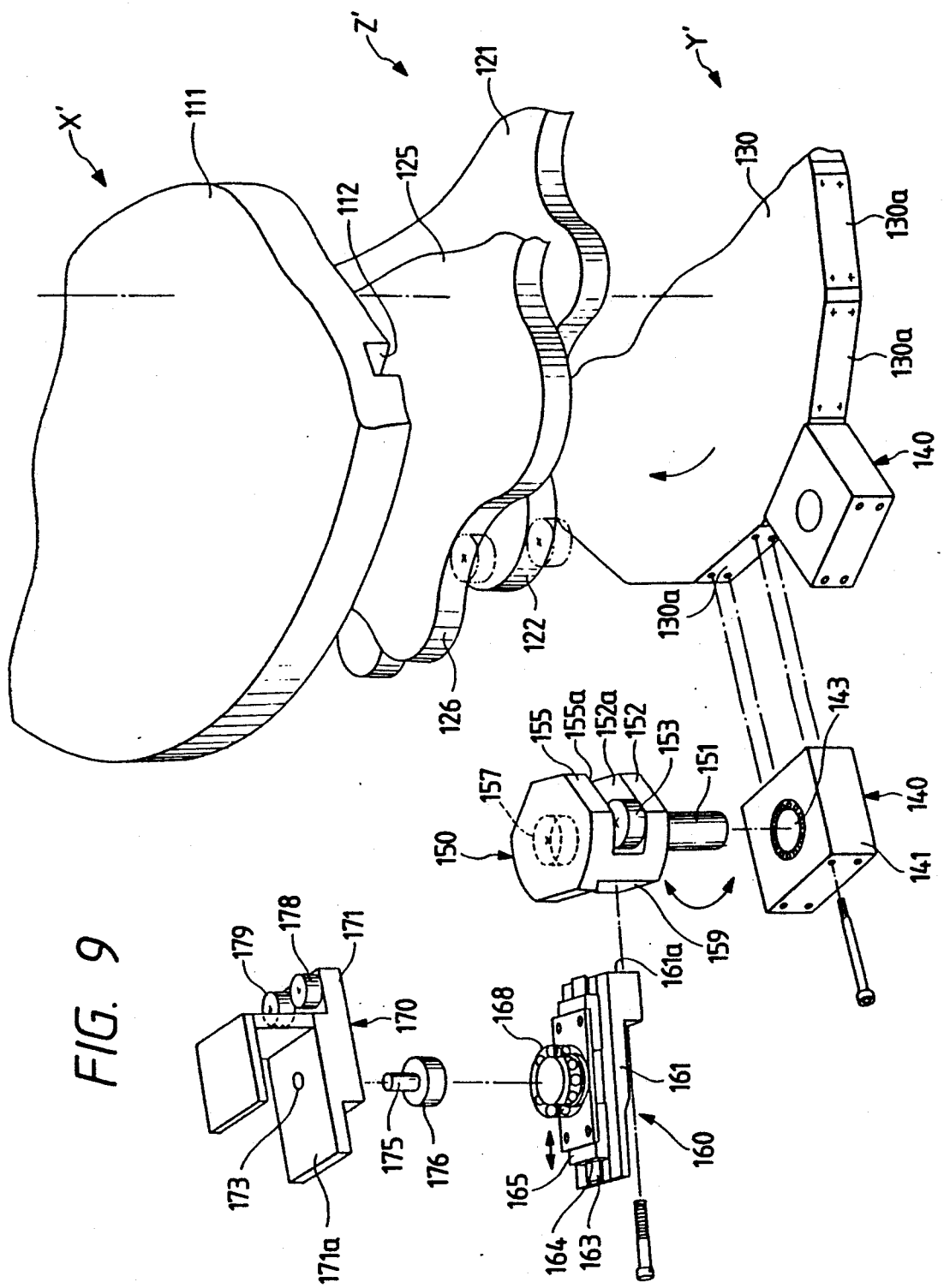
FIG. 9 is a disassembled perspective view of a rotary index apparatus according to another embodiment of the present invention.

Referring to FIG. 9 showing a disassembled perspective view of the rotary index apparatus of the second embodiment, the apparatus comprises an indexing conveyor unit X' provided with a plurality of work support tables 170, as base tables for supporting articles to be treated, a rotary disk unit Y' provided with swinging arms (having members 140, 150 and 160) for driving the work support tables 170 of the indexing conveyor unit X' and a cam unit Z' having cam members provided with cam surfaces 122 and 126 for guiding the swinging arms.

The rotary disk unit Y' comprises a polygonal plate 130 having a side surface consisting of a plurality of flat portions 130a, a plurality of bearing housings 140 each having a rectangular configuration and being secured to the polygonal plate 130, a plurality of cam follower supports 150 each mounted to be rotatable to the corresponding bearing housings 140 so as to extend upwardly, as viewed, and a plurality of linear guide members 160 each secured to a rear plate 159 of the corresponding cam follower support 150.

The polygonal plate 130 is rotated with a predetermined speed about a central shaft thereof connected to a drive means, not shown. Each of the bearing housing 140 is secured to the corresponding one flat surface 130a of the polygonal plate 130 by means of screws, for example. The bearing housing 140 comprises a bearing 143 having an inner axial hollow portion, as viewed, and a box member 141 in which the bearing 143 is accommodated. Into the axial hollow portion of the bearing 143 is fitted a shaft 151 secured to the bottom portion of the cam follower support 150, the detail of which is described hereunder.

The cam follower support 150 comprises vertically arranged lower plate 152 and upper plate 155 and a rear plate 159 connecting the lower and upper plate 152 and 155 at the rear sides thereof. The upper plate 155 has a lower surface 155a on which a cam follower 157 is mounted and the lower plate 152 has an upper surface 152a on which a cam follower 153 is mounted. These cam followers 157 and 153 are positioned at different levels so that the cam followers 157 and 153 abut against different staged cam surfaces 126 and 122 as cam guide passages of the cam unit Z', respectively. The shaft 151, described before, is secured to substantially the central portion of the lower surface of the lower plate 152 so as to extend downwardly and the extending front end of the shaft 151 is to be supported by the bearing 143 to be rotatable.

Figure 10:
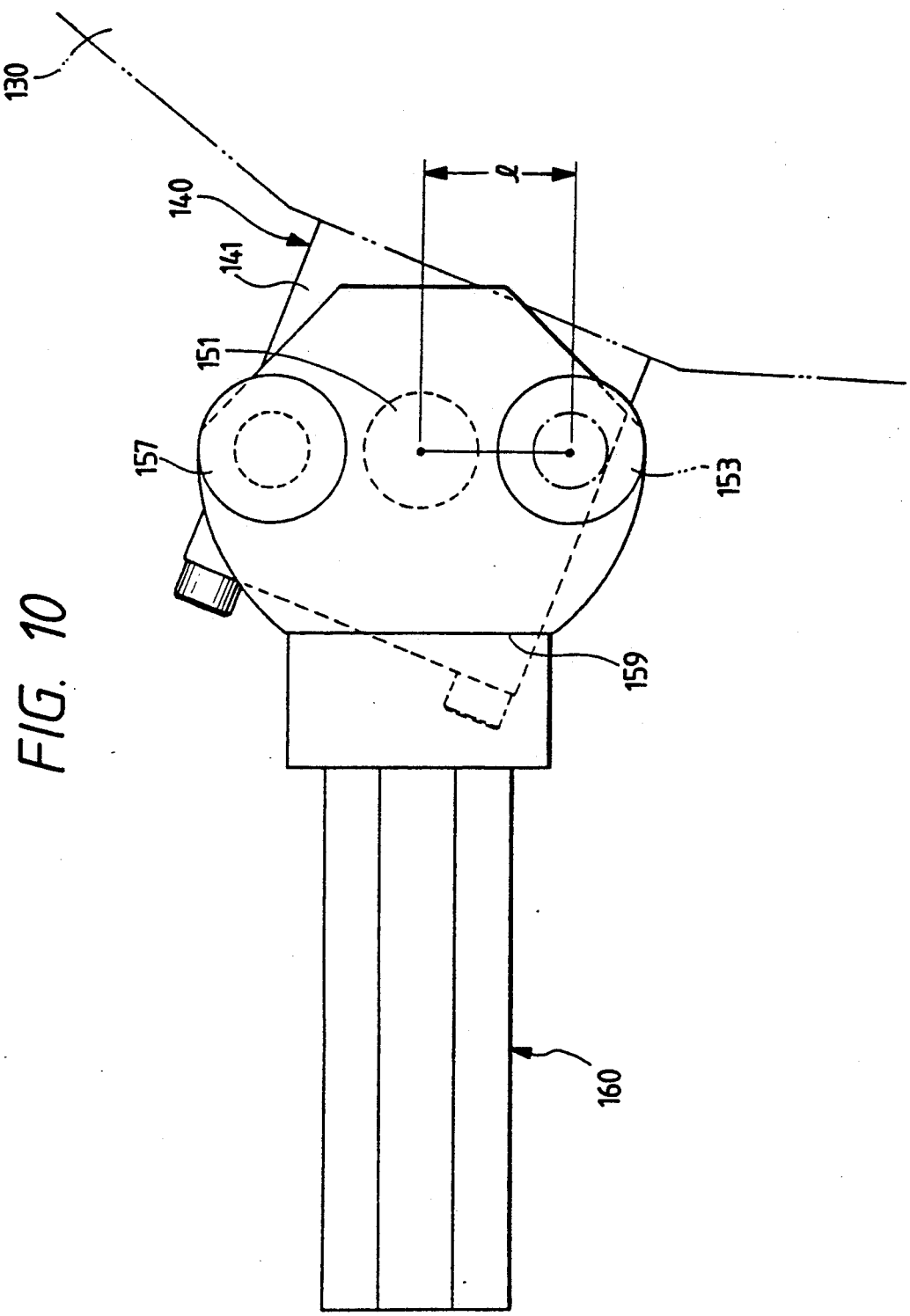
FIG. 10 is a brief plan view of a swinging arm of the second embodiment shown in FIG. 9.

The positional relationship, as viewed from the upper side in FIG. 9, between the shaft 151 and the cam followers 153 and 157 of the cam follower support 150 is shown in FIG. 10, in which the shaft 151 is positioned at substantially the central portion between the cam followers 153 and 157 which are separated by a predetermined distance in a plan view of FIG. 10. The swinging arm provided with the linear guide table 160, described hereinafter, is constructed to be swingable about the shaft 151. For example, in consideration of the relationship between one cam follower 153 and the rotating shaft 151, the relationship is substantially the same as that of the first embodiment, but in the second embodiment, in which the cam groove structure as defined in the first embodiment is not adopted, the other cam follower 157 and further cam plate 125 against which the cam follower 157 abuts are required for the substitution for the cam groove structure. In the second embodiment, only one surface of each of the two cam followers abuts against the cam surface of the cam member of the cam unit Z', thus achieving the extremely firm engagement of the cam followers with the cam surfaces and, hence, being capable of providing the rotary index apparatus operated smoothly with high speed.

To the rear plate 159 of the cam follower support 150 is secured one end of the linear guide table 160, which comprises a table body 161, a rail 163 mounted on the table body 161 and a sliding member 165 having a groove 164 which is to be slidably fitted by the rail 163. A bearing 168 having an inner hollow portion opened axially vertically is mounted on the upper surface of the sliding member 165, the bearing 168 with the hollow axial portion constituting a second engaging structure.

The cam unit Z' is arranged above the rotary disk unit Y', i.e. above the polygonal plate 130 thereof. The cam unit Z' comprises two overlapped cam plates 121 and 125 provided with cam surfaces 122 and 126, respectively, as guide passages for the cam followers 153 and 157 of the cam follower support 150. The cam surfaces 122 and 126 of the cam plates 121 and 125 are formed to have wave shapes, similar to the wave shape of the groove 22 of the first embodiment, against which the cam followers 153 and 157 abut. The two cam plates 121 and 125 of the characters described above are fixed in a manner such that the cam surfaces 122 and 126 are offset by a predetermined angle. According to the structure described above, it may be said that, in an actual operation, the cam surface of either one of the cam plates 121 and 125 attains the function substantially the same as that of the first embodiment and the other cam surface acts as a guide surface.

As shown in FIG. 9, the indexing conveyor unit X' for conveying the article to be treated such as beer bottle includes a disk-shaped base plate, for example, fixed by a fixing mechanism, not shown and the base plate 111 is provided with a ring-shaped groove 112 at the lower portion of the peripheral edge of the base plate. To the groove 112 are engaged with rollers 178 and 179 of the work support rotating member 170 to which a shaft 175 is rotatably attached. The shaft 175 has a front base end 176 which is fitted into the hollow portion of the bearing 168.

The work support rotating member 170 performing the revolving movement under the guidance of the groove 112 comprises a rotating plate 171 provided with a rest portion 171a on which a work, i.e. article, is mounted and two rollers 178 and 179 arranged at the front end portion of the rotating plate 171 and engaged with a groove 112 formed in the peripheral edge portion of the base plate 111. The rotating plate 171 is provided with an engaging hole 173 formed vertically at the central portion thereof and the shaft 175 is engaged with the engaging hole 173. As described before, the base end portion 176 of the shaft 175 serves as the second engaging structure which is engaged with the first engaging structure constituted by the bearing 168.

The second embodiment of the characters described above operates substantially the identical manner as that described with reference to the first embodiment. Namely, when one cam follower approaches a predetermined portion of the wave trough of the wave-shaped cam surface, the force for operating the second engaging structure of the rotary disk unit towards the revolving direction is vanished. In the next process, when the cam follower passes the predetermined position or the wave trough, the force for operating the second engaging structure towards the revolving direction is again generated, whereby the predetermined intermittent motion is performed.

It is to be understood that in the foregoing descriptions by way of preferred embodiment, the beer bottle inspection apparatus is explained as a typical example of the rotary index apparatus, but the present invention is not limited to the described embodiments and many other changes or modifications may be made without departing the scope of the appended claim. For example, the rotary index apparatus may be applicable to an assembling apparatus or welding apparatus in which continuous assembling or welding workings are carried out for assembling precision parts, for example.

What is claimed is:

1. A rotary index apparatus in which an article to be treated is received at an article in-conveyance position, stopped at a predetermined portion to be subjected to necessary treatment and transferred externally at an article out-conveyance position, said rotary index apparatus comprising:

an indexing conveyor means provided with a guide member along which the article received by the indexing conveyor means is conveyed with the article supported;

a rotary disk means operatively connected to said indexing conveyor means for driving the same; and a cam means operatively connected to said rotary disk means for causing an intermittent motion to said rotary disk means;

said rotary disk means including a disk plate and a plurality of swinging arms swingably secured to an outer peripheral portion of said disk plate, each of said swinging arm being provided with a cam follower and provided with a first engaging structure;

said indexing conveyor means with the guide member for guiding the revolution of the article including a plurality of work support tables arranged to a peripheral portion of said guide member, each of said work support table being arranged in positional correspondence to a respective one of said swinging arms of the rotary disk means and including a second engaging structure to be engaged with said first engaging structure of the swinging arm, and said cam means including a guide passage with which said cam follower of the swinging arm is engaged and which has a wave shape provided with predetermined alternately repeated wave troughs and wave crests so as to vanish a force for moving said second engaging structure in a revolving direction when said cam follower approaches a predetermined portion of the wave trough of the guide passage and to cause a force for moving said second engaging structure in the revolving direction when said cam follower passes the predetermined portion of the wave trough of the guide passage.

2. A rotary index apparatus according to claim 1, wherein said swinging arms are arranged along the periphery of said disk plate with equal spaces with each other.

3. A rotary index apparatus according to claim 1, wherein said first engaging structure is formed by biforked portion of the swinging arm and said second engaging structure is a guide roller secured to a lower portion of said work support table.

4. A rotary index apparatus according to claim 1, wherein said cam means includes a cam plate and said guide passage is a cam groove formed on said cam plate, said cam follower of the swinging arm being engaged with said cam groove so as to cause an intermittent movement of said work support table through the engagement between said first and second engaging structures.

5. A rotary index apparatus according to claim 1, wherein the wave shape of said guide passage of the cam means is predetermined at an article in- and out-conveyance positions so that the article is smoothly conveyed in and out of said indexing conveyor means.

6. A rotary index apparatus according to claim 1, wherein numbers of said wave troughs and wave crests of said guide passage correspond to treating stations arranged along the periphery of said guide member of the indexing conveyor means.

7. A rotary index apparatus according to claim 1, wherein said guide member is a circular track disposed along an outer periphery of the indexing conveyor means.

8. A rotary index apparatus according to claim 1, wherein said cam follower of the swinging arm is located at a portion apart from a rotation fulcrum of the swinging arm by a predetermined distance.

9. A rotary index apparatus according to claim 1, wherein said first and second engaging structures are engaged to be slidable radially of said disk plate of the rotary disk means during acceleration, deceleration and stop motions of the work support table.

10. A rotary index apparatus according to claim 1, further comprising inspecting means disposed at portions corresponding to said treating stations, respectively, for inspecting the articles to be treated and lighting means disposed at portions corresponding to the locations of said inspecting means.

11. A rotary index apparatus according to claim 10, wherein said inspecting means are cameras.

12. A rotary index apparatus according to claim 1, wherein said disk plate of the rotary disk means comprises a polygonal plate having a side surface including a plurality of flat portions and said swinging arms are secured to the flat portions of said polygonal plate, respectively, each of said swinging arms comprising a bearing housing mounted to the corresponding flat surface, a bearing incorporated in said bearing housing and having an inner axial hollow portion, a cam follower support including the cam follower to be engaged with said guide passage of the cam means and a rotating shaft to be rotatably fitted into the axial hollow portion of the bearing of the bearing housing, and a linear guide table including the first engaging structure and wherein said work support table comprises a rotating plate having a work rest member on which the article is rested, a roller means mounted to said rotating plate, said roller means being engaged with said guide member of said indexing conveyor means, and a shaft extending downwardly from a lower surface of said rotating plate, said shaft being provided with the second engaging structure and wherein said cam means comprises first and second cam plate members arranged vertically in an angularly offset manner.

13. A rotary index apparatus according to claim 12, wherein said first engaging structure comprises a bearing incorporated in said linear guide table and having an inner axial hollow portion and said second engaging structure comprises an extending front end portion of said shaft having a shape to be fitted into the axial hollow poriton of the bearing of said linear guide table.

14. A rotary index apparatus according to claim 13, wherein said first and second engaging structures are engaged to be slidable radially of said disk plate of the rotary disk means during acceleration, deceleration and stop motions of the work support table.

15. A rotary index apparatus according to claim 12, wherein said cam follower comprises first and second cam follower members arranged in upper and lower positions, respectively, said guide passage including first and second guide passages, said first and second cam plate members having side surfaces forming said guide passages engaged with said first and second cam follower members, respectively, said first and second guide passages having wave shapes respectively provided with predetermined alternately repeated wave troughs and wave crests so as to vanish a force for moving said second engaging structure in a revolving direction when one of said cam follower members approaches a predetermined portion of the wave trough of the guide passage and to cause a force for moving said second engaging structure in the revolving direction when said one of cam follower members passes the predetermined portion of the wave trough of the corresponding guide passage.

16. A rotary index apparatus according to claim 15, wherein the wave shapes of the guide passages of said first and second cam plate members are arranged in an angularly offset manner.

17. A rotary index apparatus according to claim 15, wherein numbers of said wave troughs and wave crests of each said guide passage correspond to treating stations arranged along the periphery of said guide member of the indexing conveyor means.

18. A rotary index apparatus according to claim 12, wherein said guide member of the indexing conveyor means is a groove formed in an outer periphery of the indexing conveyor means.

19. A rotary index apparatus according to claim 12, wherein the wave shapes of said guide passages of the first and second cam plate members are predetermined at an article in- and out-conveyance positions so that the article is smoothly conveyed in and out of said indexing conveyor means.

* * * * *